United States Patent [19]
Jottier

[11] 4,231,990
[45] Nov. 4, 1980

[54] APPARATUS FOR THE TREATMENT OF FLUIDS

[75] Inventor: Christian F. Jottier, Herfelingen, Belgium

[73] Assignee: S.A. Anarec, Brussels, Belgium

[21] Appl. No.: 935,293

[22] Filed: Aug. 21, 1978

[30] Foreign Application Priority Data

Aug. 31, 1977 [BE] Belgium .............................. 0180559

[51] Int. Cl.³ .......................... G01N 1/14; G01N 1/16
[52] U.S. Cl. ................................... 422/100; 73/425.6; 137/624.2; 222/71; 422/81; 422/103
[58] Field of Search .................. 422/100, 103, 63, 81; 73/421 R, 425.4, 425.6; 137/624.2; 222/71

[56] References Cited
U.S. PATENT DOCUMENTS 3,192,968  7/1965  Baruch et al. ................... 422/100 X
3,192,969  7/1965  Baruch et al. ................... 422/100 X Primary Examiner—R. E. Serwin
Attorney, Agent, or Firm—Sughrue, Rothwell, Mion, Zinn and Macpeak

[57] ABSTRACT

A reactor for preparing and analyzing fluids comprising means for taking a determined dose of a sample and transferring it in an air-tight chamber, means for taking, if necessary, a determined dose of a diluent and transferring it in the same chamber, means for taking at least one determined dose of a reagent and for transferring it in the same chamber, means for mixing the sample with the reagent or the reagents together with a diluent (if necessary) out of contact with the atmosphere, as well as means for transferring the obtained mixture of solutions to any system for detecting the result or for transferring part of said mixture to another reactor or to another use device.

9 Claims, 3 Drawing Figures

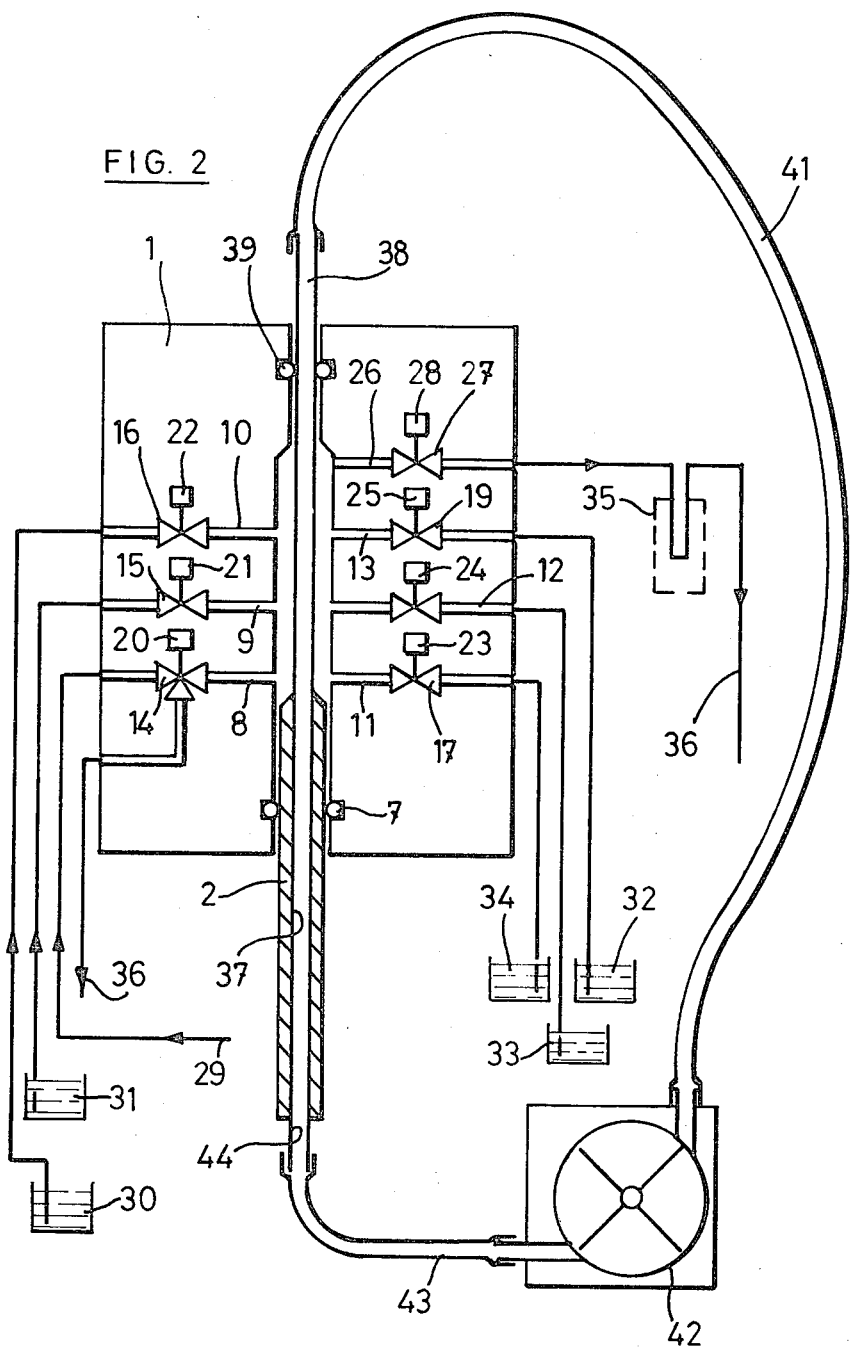

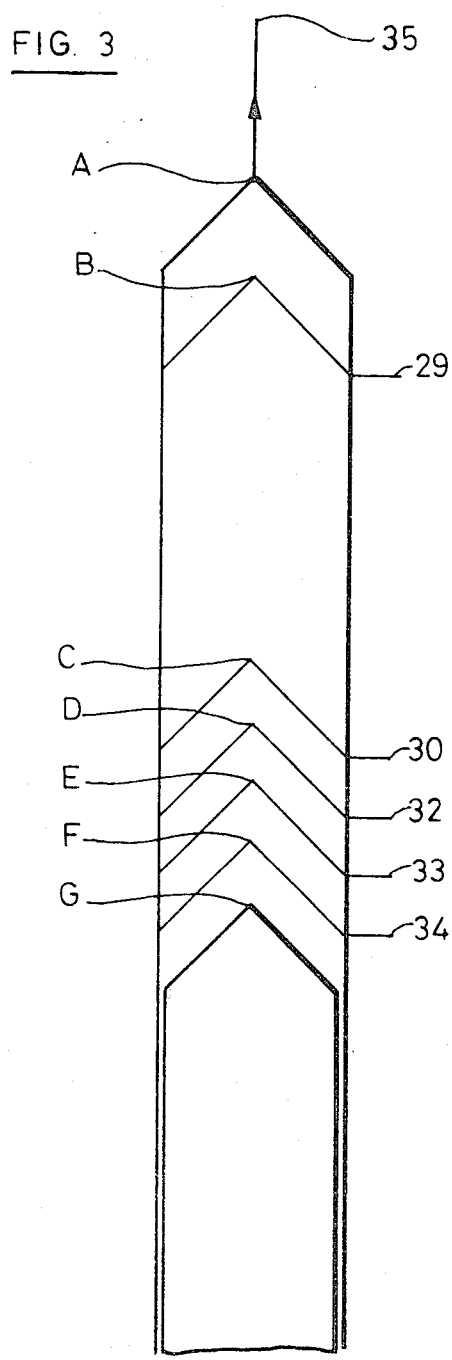

APPARATUS FOR THE TREATMENT OF FLUIDS

BACKGROUND OF THE INVENTION

Apparatuses for the treatment of fluids, such as automatic apparatuses for analysis or reactions using chemical products, are known. These known apparatuses frequently have drawbacks. Thus, in the known analysis apparatuses, the mixing of the sample to be analyzed with the reagent or reagents generally takes place in an atmospheric medium. Moreover, said known apparatuses commonly need distinct means for taking the sample to be analyzed, for distributing the reagent or reagents, and for diluting and conveying the obtained mixture or solution to the detection or treatment device.

BRIEF DESCRIPTION OF THE INVENTION

An object of this invention is an apparatus for the automatic treatment of fluids, in which all the processing steps are performed under shelter of the atmosphere according to a predetermined sequence or program.

The term "treatment", as used in the present specification and claims, means any physical or chemical process, in which at least two fluids are contacted with each other. Among such treatments may be cited, as non limitative examples, the mixing of fluids, the analysis of chemical products (liquids and gases or solids), the synthesis of chemical compounds and the like.

The term "fluid", as used in the present specification and claims, means a liquid, an emulsion or suspension of a solid in a liquid, a gas and even a powdered and/or pourable solid.

The apparatus for the treatment of fluids according to this invention comprises an air-tight treatment chamber, a piston adapted for varying the volume of said chamber, means for operating the piston, at least two pipes or ducts, which are each equipped with a valve, which are connected to a fluid source and each of which open into said treatment chamber and an outlet pipe from the chamber equipped with a valve, the fluids being brought into the treatment chamber by an aspiration or depression created in said chamber by a movement of the piston.

According to a complementary feature of the apparatus according to this invention, this apparatus also comprises a pipe or duct which is equipped with a valve and which allows the connection of the treatment chamber with the atmosphere. Preferably, the apparatus according to this invention comprises several ducts or pipes each equipped with a valve and opening in the chamber at different levels, each of said valves being advantageously controlled by electrical, pneumatic, hydraulic or similar means according to a predetermined sequence or program.

The apparatus according to this invention may also comprise means for regulating the temperatures of the chamber content, said means preferably comprising a closed circuit in which a heating or cooling fluid flows, said circuit extending axially in the piston and in the treatment chamber, a heat exchanger being provided in said circuit, as well as means for causing the heating or cooling fluid to flow into said closed circuit.

BRIEF DESCRIPTION OF THE DRAWINGS

Other details and features of the invention will appear in the following description of embodiments of the apparatus according to this invention, said embodiments being described by way of non limitative examples.

In said description, reference is made to the attached drawings, in which:

FIG. 2 shows also diagrammatically a second embodiment of an apparatus according to this invention, and FIG. 3 illustrates a mode of operation of the apparatus represented in FIG. 1.

In the various figures, the same references are used for designating identical or similar elements.

DETAILED DESCRIPTION OF THE INVENTION

Figure 1:
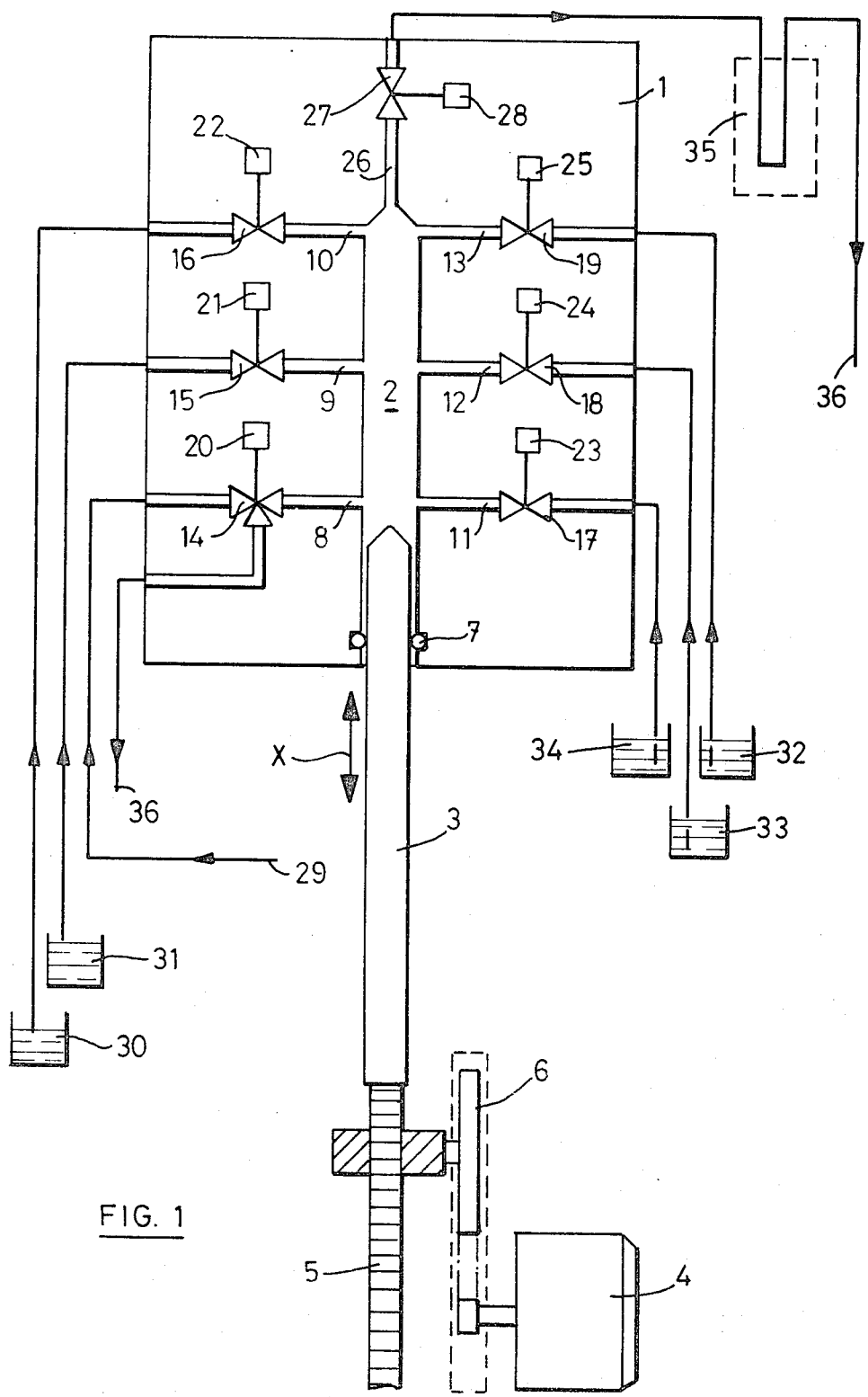
FIG. 1 shows diagrammatically a first embodiment of an apparatus according to this invention.

In the following description, the invention is illustrated by an analysis apparatus, but it must be understood, as already pointed out, that the invention is not limited to such an analysis apparatus and may be used for other physical and/or chemical operations or processes.

The apparatus represented in FIG. 1 comprises a body 1 which contains a chamber 2, wherein a piston 3 may be subjected to a linear or reciprocating movement by a step-by-step motor 4, by means of a rack system 5 and a speed-reducing gear 6.

A packing 7 is provided for maintaining tightness between the inner wall of the chamber 2 and the piston 3.

In the wall of the chamber 2 of the apparatus are provided six pipes or ducts 8, 9, 10, 11, 12 and 13, each of said ducts being equipped with a valve 14, 15, 16, 17, 18 and 19 controlled, in the illustrated example, by six step-by-step motors 20, 21, 22, 23, 24 and 25.

A duct 26 formed in the free conical end of the chamber 2 connects said chamber with the exterior by means of a two-way valve 27 operated by a step-by-step motor 28.

The apparatus shown in FIG. 1 allows, for example, the performance of an automatic chemical analysis, with the possibility of diluting or dissolving previously the sample to be analyzed and with the possibility of using three different reagents.

Moreover, the calibration of the apparatus may be effected by introducing into the treatment chamber 2 a standard instead of the sample to be analyzed.

A source 29 of the sample to be analyzed is connected to valve 14, a source 30 of a dilution agent or solvent to valve 16, a source 31 of calibration or standardization solution to valve 15, a source 32 of the first reagent to valve 34, a source 33 of the second reagent to valve 18 and a source 34 of the third reagent to valve 17.

FIGS. 1 and 3 illustrate schematically a program of the apparatus, described by way of example.

The taking of the sample is performed by opening valve 14 and by displacing the piston 3 by a predetermined stroke AB which corresponds to the volume needed for the analysis. The dilution with automatic mixing of the diluent with the sample is made by opening valve 16 and by displacing the piston 3 on the predetermined stroke BC which corresponds to the volume needed for the analysis.

The needed amount of the first reagent is introduced into the chamber 2 by opening valve 19 and by moving the piston 3 on a stroke CD which corresponds to the volume of said reagent necessary for the analysis.

The mixing of the first reagent with the diluted sample is effected by moving the piston 3 from D to G and returning it to the D position, all the valves being closed. Alternately, the mixing step may be carried out by admitting a volume of gas into the treatment chamber after inducing a vacuum in the chamber.

A reaction period, which can be regulated in accordance with the method used, is provided in the automatic program.

The necessary amount of the second reagent is introduced into chamber 2 by opening valve 18 and displacing piston 3 on stroke DE corresponding to the volume needed for the analysis.

The mixing of the second reagent with the diluted sample and with the first reagent is performed by moving piston 3 from E to G and returning it to the E position, all the valves being closed.

A new reaction period, which may be regulated in accordance with the selected method, is provided in the automatic operation program of the apparatus.

The needed amount of the third reagent is introduced into chamber 2 by opening valve 17 and displacing piston 3 along stroke EF corresponding to the volume necessary for the analysis.

The mixing of the third reagent with the diluted sample and with the first and second reagents is performed by moving piston 3 from F to G and returning it to the F position.

A new reaction period of time, which can be regulated in accordance with the selected method of analysis is provided in the operation program of the apparatus.

The transfer of the reaction medium towards a detection device 35 is effected by opening valve 27 and by moving the piston 3 on stroke FA corresponding to the total of the volumes of sample, diluent, and reagents introduced in the chamber 2 by the successive displacements of the piston controlled by motor 4.

When the analysis is finished, chamber 2 may be rinsed or washed by opening valve 16 (dilution water) and by moving the piston 3 on the maximum stroke AG.

The rinsing or washing solution is sent to a sewage 36 by returning the piston to position A. If necessary, the rinsing or washing may be performed several times.

The standardization is performed in the same way as described above, sample 19 being merely replaced by a standard sample 31, valve 15 being opened instead of valve 14 and the displacement of the piston 3 being effected along an identical stroke AB.

In the second embodiment of the invention, the apparatus is equipped with means for regulating the temperature of the content of chamber 2. These means consist of a closed circuit in which a cooling or heating fluid (such as water or an organic liquid) flows. Said closed circuit comprises an axial bore 37 in the piston 2, a rigid tube 38 being connected to said bore 37, whereas a packing ring 39 is provided at the outlet of the rigid tube 38 from the chamber 2. At the end of the rigid tube 38 is connected a flexible pipe 41 which is connected to a heat exchanger diagrammatically shown in 42. This heat exchanger comprises a heating or cooling element and a pump. The outlet of the heat exchanger 42 is connected, also by means of a flexible pipe 43, to a rigid tube 44 connected to the bore 37 of piston 2.

Due to the fact that pipes 41 and 43 are flexible, the piston 2 and the rigid tube 40 which is fixed to it can move alternately in the direction of arrows X under the control of the motor 4, rack or worm 5 and speed-reducing gear 6.

As stated above, the invention relates to a reactor for the treatment of fluids, for example for preparing and analyzing purposes, said reactor comprising means for taking a determined dose of a sample and transferring it in an air-tight chamber, means for taking, if necessary, a determined dose of a diluent and transferring it in the same chamber, means for taking at least one determined dose of a reagent and for transferring it in the same chamber, means for mixing the sample with the reagent or the reagents together with a diluent (if necessary) out of contact with the atmosphere, as well as means for transferring the obtained mixture of solutions to any system for detecting the result or for transferring part of said mixture to another reactor or to another use device.

The steps of volumetrically taking samples, the dosage of precise volumes of the reagent or reagents, the dilution of the samples, the transfer of the obtained mixture toward a detection or other use device are performed by means of a single piston which accomplishes all the functions hereabove described.

An electronic or pneumatic logic or other active programmation, a step-by-step motor, a pneumatic jack or any other means allows the control of the movements of said piston in proportion to the volumes and the chronology necessary for the reactions or the preparation.

The apparatus according to this invention may be used for example for the analysis of liquid, gaseous and solid samples in plants for distributing water (determination of the hardness of water, fluor, dissolved oxygen, chlorine, etc.), in plants for purifying water (analysis of silica, iron, $SO_4^{--}$ ions, etc.), in plants for the control of gaseous or liquid industrial effluents in order to prevent the pollution of rivers and atmosphere, in the metallurgical industry (analysis of ores), in the chemical industry in general (control or analysis of synthetized products), in the medical field (analysis of body liquids, such as blood and urine).

The apparatus according to this invention may be used for calorimetric, conductimetric, thermochemical analysis and the like, for detecting mineral elements (such as iron, cobalt, aluminium, calcium, copper, magnesium, manganese, nickel, chromium, mercury, lead, bismuth, zinc, fluorine, chlorine, iodine, arsenic; nitrate, nitrite, sulphate, chloride, sulphite, cyanide, phosphate, sulphide ions, etc.), or organic compounds (such as formaldehyde, carbon tetrachloride, carbon sulphide, chloroform, hydrazine, detergents, sugars, carbon dioxide, carbon monoxide, acrylic monomers, styrene, benzene, toluol, xylol, etc.).

The apparatus according to this invention may also be used for the synthesis or extraction of chemical compounds on a laboratory scale, in a pilot plant or even on an industrial scale.

Contrary to the systems and devices used until now, the apparatus according to this invention allows the control, by means of an automated generating system, of a series of analysis and/or synthesis steps which can easily be determined in advance. Indeed, the conception of the apparatus allows the use thereof for controlling automatically a great number of chemical analysis and other reactions.

What I claim is:

1. An apparatus for the treatment of fluids comprising a single air-tight chamber having a variable inner volume, in which at least two fluids may be introduced and treated and from which the fluids may be removed after treatment, a reciprocable piston which tightly closes one end of said chamber, at least two inlet pipes or ducts connected at one end to said chamber and at the other end to a fluid source, a valve being inserted in each of said inlet pipes or ducts near the end thereof connected to said chamber, an outlet pipe equipped with a valve near the end thereof connected to said chamber, means for moving the reciprocable piston and means for selectively opening and closing the valves inserted in said inlet and outlet pipes, a predetermined amount of each fluid being selectively introduced into said chamber via said selectively opened valves inserted in said inlet pipes or ducts by means of a depression or suction created in said chamber, said moving means being operable to move said piston along a predetermined stroke in a direction causing an increase in the inner volume of said chamber to create said suction, the treatment of the fluids in the chamber being effected when all the valves inserted in the inlet and outlet pipes are closed, and the removal of the treated fluids from the treatment chamber being effected via said selectively opened valve inserted in said outlet pipe by the pressure created in said chamber by the piston when the latter is moved in an opposite direction causing such a decrease of the inner volume of the chamber that said inner volume is entirely occupied by the piston.

2. Apparatus according to claim 1, wherein said means for moving the piston comprises a step-by-step motor acting on the piston through a rack system.

3. Apparatus according to claim 1, wherein the fluids treated in said chamber are mixed by repeatedly reciprocating said piston when all the valves inserted in the inlet and outlet pipes are closed.

4. An apparatus according to claim 1, wherein the fluids treated in said chamber are mixed by creating an additional depression or suction in the chamber so as to admit a gas from a pipe connected at one end to said chamber and to its other end to a gas source via a valve inserted in the pipe near the end thereof connected to the chamber.

5. An apparatus according to claim 1, and further comprising rinsing means comprising a pipe or duct connected at one end to a source of rinsing or washing liquid and at the other end to said chamber, a valve being inserted in said pipe near the end thereof connected to the chamber.

6. An apparatus according to claim 1, in which the fluid source to which one of said inlet pipes is connected is a source of a fluid to be analyzed.

7. An apparatus according to claim 6, in which the fluid source to which one of the inlet pipes is connected is a source of a reagent for treating the fluid to be analyzed.

8. An apparatus according to claim 1, and further comprising means for controlling the temperature of the contents of the treatment chamber.

9. An apparatus according to claim 8, in which the means for controlling the temperature of the chamber contents comprises a closed fluid circuit including a heat exchanger, through which a heating or cooling fluid is caused to flow, said circuit having a part extending axially through the piston and the chamber.

* * * * *